(12) United States Patent
Piepenburg et al.

(10) Patent No.: US 8,022,194 B2
(45) Date of Patent: *Sep. 20, 2011

(54) 2'-NITROBENZYL-MODIFIED RIBONUCLEOTIDES

(75) Inventors: Olaf Piepenburg, Barnet (GB); Derek L. Stemple, St. Albans (GB); Niall A. Armes, Fulbourn (GB)

(73) Assignee: Alere San Diego, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/803,261

(22) Filed: Jun. 21, 2010

(65) Prior Publication Data

US 2011/0053154 A1 Mar. 3, 2011

Related U.S. Application Data

(63) Continuation of application No. 11/628,343, filed as application No. PCT/IB2005/002488 on Jun. 2, 2005, now Pat. No. 7,759,061.

(60) Provisional application No. 60/576,907, filed on Jun. 2, 2004.

(51) Int. Cl.
| | |
|---|---|
| C07H 21/02 | (2006.01) |
| C07H 21/04 | (2006.01) |
| C07H 21/00 | (2006.01) |
| C07H 19/04 | (2006.01) |
| C12Q 1/68 | (2006.01) |
| C12P 19/34 | (2006.01) |

(52) U.S. Cl. ......... 536/23.1; 435/6; 435/91.1; 536/24.3; 536/25.3; 536/26.6

(58) Field of Classification Search ............. 435/6, 91.1; 536/23.1, 24.3, 25.3, 26.6
See application file for complete search history.

(56) References Cited

U.S. PATENT DOCUMENTS

| | | |
|---|---|---|
| 5,536,649 A | 7/1996 | Fraiser et al. |
| 6,136,543 A | 10/2000 | Anazawa et al. |
| 7,759,061 B2 * | 7/2010 | Piepenburg et al. ............. 435/6 |

FOREIGN PATENT DOCUMENTS

| | | |
|---|---|---|
| EP | 0 624 643 | 4/1994 |
| WO | WO 91/17267 | 11/1991 |
| WO | WO 00/53805 | 9/2000 |
| WO | WO 03/072805 | 9/2003 |
| WO | WO 2005/118853 | 12/2005 |

OTHER PUBLICATIONS

International Search Report, for the corresponding PCT Application No. PCT/IB2005/002488, dated Feb. 10, 2006.

Astatke et al., "A single side chain prevents *Escherichia coli* DNA polymerase I (Klenow fragment) from incorporating ribonucleotides," Proc. Natl. Acad. Sci., 95:3402-3407, 1998.

Brieba and Sousa, "Roles of Histidine 784 and Tyrosine 639 in Ribose Discrimination by T7 RNA Polymerase," Biochem., 39(5):919-923, 2000.

(Continued)

*Primary Examiner* — Jezia Riley
(74) *Attorney, Agent, or Firm* — Fish & Richardson P.C.

(57) ABSTRACT

This disclosure provides novel reversibly terminated ribonucleotides which can be used as a reagent for DNA sequencing reactions. Methods of sequencing nucleic acids using the disclosed nucleotides are also provided.

23 Claims, 4 Drawing Sheets

2'-2-Nitrobenzyl-ATP

2'-desyl-ATP

2'-p-hydroxyphenacyl-ATP

OTHER PUBLICATIONS

Cech, "Structure and Mechanism of the Large Catalytic RNAs: Group I and Group II Introns and Ribonuclease P," *The RNA World*, 239-269, 1993.

Conrad et al., "Enzymatic synthesis of 2'-modified nucleic acids: identification of important phosphate and ribose moieties in RNase P substrates," Nucleic Acids Res., 23(11):1845-1853, 1995.

Gao et al., "Conferring RNA polymerase Activity to a DNA polymerase: A single residue in reverse transcriptase controls substrate selection," Proc. Natl. Acad. Sci., 94:407-411, 1997.

Givens et al., "New Photoprotecting Groups: Desyl and p-Hydroxyphenacyl Phosphate and Carboxylate Esters," Methods Enzymol. 291:1-29, 1998.

Johnson et al., "Processive DNA synthesis observed in a polymerase crystal suggests a mechanism for the prevention of frameshift mutations," Proc. Natl. Acad. Sci., 100(7):3895-3900, 2003.

Metzker et al., "Termination of DNA synthesis by novel 3'-modified-deoxyribonucleoside 5'-triphosphates," Nucl. Acids Res., 22(20):4259-4267, 1994.

Milligan et al., "Oligoribonucleotide synthesis using T7 RNA polymerase and synthetic DNA templates," Nucleic Acids Res., 15(21):8783-8798, 1987.

Padilla and Sousa, "A Y639F/H784A T7 RNA polymerase double mutant displays superior properties for synthesizing RNAs with non-canonical NTPs," Nucleic Acids Res., 30(24):e138 (1-4), 2002.

Raap, "Advances in fluorescence in situ hybridization," Mutat. Res., 400:287-298, 1998.

Saiki et al., "Primer-Directed Enzymatic Amplification of DNA with a Thermostable DNA Polymerase," Science, 239:487-491, 1988.

Sanger et al., "DNA sequencing with chain-terminating inhibitors," Proc. Natl. Acad. Sci., 74(12):5463-5467, 1977.

Shin et al., "Synthesis and Photoaffinity Labeling of 3'(2')-O-(p-azidobenzoyl) ATP," J. Biochem. Mol. Biol., 30(3):211-215, 1997.

Sioud and Sorensen, "A nuclease-resistant protein kinase Cα ribozyme blocks glioma cell growth," Nat. Biotechnol., 16:556-561, 1998.

Song and Kang, Sequence-specific termination by T7 RNA polymerase requires formation of paused conformation prior to the point of RNA release, Genes to Cells., 6:291-301, 2001.

Tabor and Richardson, "A single residue in DNA polymerases of the *Escherichia coli* DNA polymerase I family is critical for distinguishing between deoxy- and dideoxyribonucleotides," Proc. Natl. Acad. Sci., 92:6339-6343, 1995.

Temiakov et al., "Characterization of T7 RNA Polymerase Transcription Complexes Assembled on Nucleic acid Scaffolds," J. Biol. Chem., 277(49):47035-47043, 2002.

Van Ness et al., "Isothermal reactions for the amplification of oligonucleotides," Proc. Nat. Acad. Sci. USA, 100(8):4504-4509, 2003.

Yin and Steitz, "The Structural Mechanism of Translocation and Helicase Activity in T7 RNA Polymerase," Cell, 116(3):393-404, 2004.

\* cited by examiner

2'-2-Nitrobenzyl-ATP    2'-desyl-ATP    2'-p-hydroxyphenacyl-ATP

*-AACUGCGGCGAU
　　　　　CGCCGCTATCCATAAAGTCTGTCCTGGG

< 11nt
< 10nt
< 9nt
< 8nt 1   2   3   4

2'-NITROBENZYL-MODIFIED RIBONUCLEOTIDES

RELATED APPLICATIONS

This application is a continuation of U.S. patent application Ser. No. 11/628,343, filed Aug. 16, 2007 now U.S. Pat. No. 7,759,061, which is a National Stage of International Application No. PCT/IB2005/002488, filed Jun. 2, 2005, which claims the benefit of priority to U.S. Provisional Application No. 60/576,907, filed Jun. 2, 2004, the contents of each of which are hereby incorporated by reference in their entireties.

BACKGROUND

In-vivo RNA and DNA polymerases utilize ribonucleotides and deoxyribonucleotides respectively, for the polymerisation of nucleic acids, and discriminate between these nucleotides with high fidelity. Extensive efforts have been made to permit the incorporation of modified nucleotides by polymerases, including base modifications, sugar modifications, and backbone modifications. The use of such modified nucleotides as substrates for both RNA- and DNA-polymerases is desirable for a variety of reasons. Among others these include the incorporation of fluorescent labels for product detection (Raap), ribose-modified nucleotides for the generation of polynucleotides less susceptible to nuclease action (Sioud) or the use of terminating dideoxyribose nucleotides for DNA sequencing (Sanger).

Attempts to use modified nucleotides are often hampered by the substrate specificity of the polymerase in question. Modification with additional chemical moieties on the base have on the whole met with good success providing that the additional groups are attached to non Watson-Crick pairing residues and project out of the major groove. On the other hand modifications of the sugar rings have proven to be much less well tolerated presumably reflecting the presence of exquisitely precise interactions between the sugar and the enzyme during nucleotide binding and catalysis. Nevertheless there are several notable successes of the employment of mutagenesis to engineer polymerases capable of improved capacity to use sugar-modified nucleotides. In the case of DNA sequencing, polymerases have been improved in their utilisation of 2'3'-dideoxynucleotide terminators by engineering an amino acid substitution in the active site rendering the polymerase more similar to T7 DNA polymerase, demonstrated to tolerate such nucleotides well (Tabor).

Furthermore investigation into the biochemical and structural source of differing substrate specificity between bacterial and phage DNA and RNA polymerases has lead to the identification of residues which if substituted enable RNA polymerases to use deoxyribonucleotides, and others that allow DNA polymerases to use ribonucleotides. In particular a peptide loop referred to as the 'steric gate' appears to prevent DNA polymerases from accepting groups bulkier than the lone hydrogen atom present at the 2' position in deoxyribonucleotides. This loop is essentially missing in phage-encoded RNA polymerases. On this basis there is reason to believe that RNA polymerases may be somewhat more tolerant to the presence of other groups attached to the 2' position of the sugar ring providing the groups are relatively small. Consistent with this Padilla and Sousa have shown that T7 RNA polymerase is capable of utilising nucleotides modified at the 2' position with O-methyl groups, or with azido (N3) groups (Padilla), provided that one or two additional enabling amino acid substitutions are also introduced.

BRIEF DESCRIPTION OF THE INVENTION

The invention is based on the discovery of novel reversibly terminated ribonucleotides and methods for using these novel nucleotides for sequencing nucleic acids.

One aspect of the invention is directed to a ribonucleoside having a formula SM-BASE wherein SM is a ribose, BASE is a pyrimidine or purine, and wherein said ribose comprises a reversible chain terminating moiety at a 2' position in said ribose. See FIG. 1 for an example of such a ribonucleoside (ribonucleotide or ribonucleoside 5' triphosphates). The BASE may be, for example, adenine, guanine, cytosine or uracil. The ribonucleoside may be a ribonucleoside 5'-phosphate, a ribonucleoside 5'-diphosphate or a ribonucleoside 5'-triphosphate—with a structure of PM-SM-BASE wherein PM is a phosphate moiety (e.g., monophosphate, diphosphate, or triphosphates).

One advantage of the nucleotides of the invention is that it can serve as a chain termination nucleotide. That is, the incorporation of the nucleotide into an elongating nucleic acid chain prevents the subsequent incorporation of any additional nucleotide to the same chain by a polymerase.

It is understood that the ribonucleosides of the invention also encompass ribonucleotides—which are phosphate esters of ribonucleosides. Thus, the ribonucleosides of the invention can be a ribonucleotide. Examples of such ribonucleotides include adenosine 5'-monophosphate (adenylate or AMP), adenosine 5'-diphosphate (ADP), adenosine 5'-triphosphate (ATP), guanosine 5'-monophosphate (guanylate or GMP), guanosine 5'-diphosphate (GDP), guanosine 5'-triphosphate (GTP), uridine 5'-monophosphate (uridylate or UMP), uridine 5'-diphosphate (UDP), uridine 5'-triphosphate (UTP), cytidine 5'-monophosphate (cytidylate or CMP), cytidine 5'-diphosphate (CDP), and cytidine 5'-triphosphate (CTP).

The reversible chain terminating moiety may be connected to a ribonucleoside or ribonucleotide of the invention by a reversible linkage. The reversible linkage may be a bond that is cleavable by electromagnetic radiation, chemical treatment or combination of these treatments. For example, the treatment may be a exposure to electromagnetic radiation such as light (UV light).

Examples of suitable reversible chain terminating moiety include a 2-Nitrobenzyl group, a Desyl group or a p-hydroxyphenacyl caging group (See FIG. 1).

In addition, the ribonucleosides and ribonucleotides of the invention may comprise a detectable label. The detectable label may be a detectable moiety such as green fluorescent protein, blue fluorescent protein, red fluorescent protein, beta-galactosidase, chloramphenicol acetyltransferase, beta-glucoronidase, luciferases, b-lactamase, digoxygenin, fluorescent dye molecule, fluorescein, cy3, cy5, alkaline phosphatase, horse radish peroxidase or a combination of these moieties.

In a preferred embodiment, the detectable label is removable. The detectable label may be removable by photobleaching. Alternatively, the detectable label may be connected to the ribonucleotide by a reversible linkage. The reversible linkage may be a bond that is cleavable by electromagnetic radiation, chemical treatment, or a combination of these treatments.

Another embodiment of the invention is directed to a method for producing a reversibly terminating ribonucleoside. The ribonucleoside may be a ribonucleoside 5' monophosphate, ribonucleoside 5' diphosphate, or a ribonucleoside 5' triphosphates. The method comprises a first step of providing a ribonucleoside having a formula SM-BASE wherein SM is a ribose, BASE is a pyrimidine or purine. In the second step, a reversible chain terminating moiety is attached to a 2' position of the ribose. The reversible chain termination moiety may be a 2-Nitrobenzyl group, a Desyl group or a p-hydroxyphenacyl caging group.

Another aspect of the invention is directed to a method of sequencing a nucleic acid using the ribonucleosides/ribonucleotides of the invention. In the method, a primer (which may be DNA or RNA) is complexed (i.e., hybridized by base pairing) with a target nucleic acid and elongated with an RNA polymerase and one first species of ribonucleotide (e.g., ATP, GTP, CTP or UTP) having the formula PM-SM-BASE wherein PM is a phosphate moiety, SM is a ribose, BASE is a pyrimidine or purine, wherein said ribose comprises a chain terminating moiety connected by a reversible linkage at a 2' position of said ribose. In the second step, the incorporated ribonucleotide is detected to determine a sequence of said target nucleic acid. In an optional step, the chain terminating moiety of the incorporated ribonucleotide may be removed by removing the reversible linkage. Optionally, these steps are repeated with at least a second species of ribonucleotide with the same chemical structure but a different base.

The primer/target nucleic acid complex may be formed by hybridizing two nucleic acids strands or by synthesis by RNA polymerase. For example, T3 RNA polymerase, T7 RNA polymerase, and SP6 RNA polymerase can synthesize RNA primers de novo at a proper RNA promoter sites (i.e., at the proper DNA sequences). Thus, a primer:target nucleic acid complex may be made by contacting a T7 polymerase with a DNA molecule which contains the a T7 promoter sequence along with NTPs.

The RNA polymerases referred to in this disclosure may be any RNA polymerase and include, at least, a phage-encoded RNA polymerase such as T3 RNA polymerase, T7 RNA polymerase or SP6 RNA polymerase.

The polymerases of this disclosure may include a deletion or substitution in the steric gate region or in the nucleotide binding and catalytic pocket region. With these deletions and substitutions, a DNA polymerase may be used for the methods of the invention.

Another aspect of the invention is directed to a method of sequencing a target nucleic acid comprising the steps of (1) elongating a primer which is complexed with a target nucleic acid with a RNA polymerase and ribonucleotides ATP, GTP, UTP, and CTP to form an incorporated nucleotide, wherein said ribonucleotides have the formula PM-SM-BASE wherein PM is a phosphate moiety, SM is a ribose, BASE is a pyrimidine or purine, wherein said ribose comprises a chain terminating moiety connected by a reversible linkage at a 2' position of said ribose and wherein each of said ribonucleotide is reversibly labeled with a detectable label; and (2) detecting said incorporated nucleotide by detecting said detectable label to determine a sequence of said target nucleic acid. This method can further comprise the optional steps of removing the chain terminating moiety and said detectable label from the incorporated ribonucleotide. These steps may be repeated until a desired amount of nucleic acid sequence is determined.

It is understood that the term "2' modified ribonucleotide," as used in this disclosure, refers to a novel 2' modified ribonucleotide as described in this disclosure. Unless otherwise indicated, a 2' modified ribonucleotide includes a ribonucleotide comprising a reversible 2' modification. The reversible modification may be removed, for example, by exposure of the 2' modified nucleotide to electromagnetic radiation— including ultraviolet light. One embodiment of a 2' modified ribonucleotide is shown in FIG. 1.

DETAILED DESCRIPTION OF THE INVENTION

Figure 1:
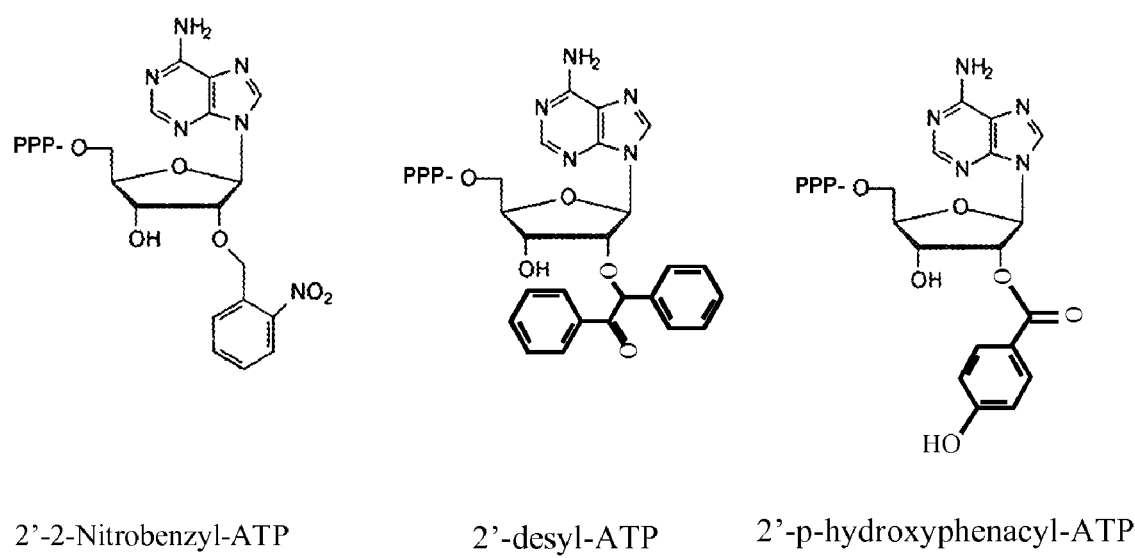
FIG. 1 depicts the chemical structure of 2'-2-Nitrobenzyl-ATP, 2'-desyl ATP and 2'-p-hydroxyphenacyl-ATP. The adenosine base may be substituted with any other base such as guanosine, uridine, or cytidine. The chemical structure is PM-SM-BASE where PM is a phosphate group or moiety, SM is a sugar group or moiety and BASE is pyrimidine or purine.

We have previously devised a strategy for performing direct sequencing of single DNA molecules (WO 00/53805). This method is reliant on the use of nucleotides which function as reversible terminators, most likely enabled by modification of the sugar ring reversible by light or chemical environment (other configurations may also be possible). Furthermore it ideally requires the use of processive polymerase enzymes as release of the template under study would cause it to be released from the physical location at which the sequencing reaction is occurring. Accordingly we have begun studies employing polymerases known to be processive in character, and have identified T7 RNA polymerase (and its relatives in other phages such as T3 and SP6) as ideal for our purposes. These polymerases combine high processivity with the possibility of greater flexibility for the use of sugar-modified nucleotides. Furthermore as they function on double-stranded DNA, naturally unzip and then re-zip the helix behind them, they obviate some of the difficulties encountered in assembling processive DNA polymerases, and the fact that such DNA polymerases are rarely strand displacing and/or difficulties may occur in the preparation of single-stranded templates.

For the purposes of our studies we have employed several different assays for the utilisation of nucleotides by T7 RNA polymerase and variants that we have engineered. T7 RNA polymerase can incorporate ribonucleotides into a growing chain in at least two different synthetic modes. When the polymerase recognises a bona fide promoter sequence it initiates the synthesis of short runs of RNA in a distributive mode, but in a template-dependent manner. The polymerase may slip back and forth releasing short RNA fragments, but eventually locks onto the template in a new stable mode known as the elongation mode. Additionally T7 RNA polymerase has been reported to add a nucleotide to the transcript when it reaches the very end of a template in a non-template directed manner. Finally, whilst T7 RNAP normally works in the context of a promoter element encoded in the template as described, a model system has been devised by Temiakov et al. (Temiakov), in which the RNA polymerase extends the RNA chain of a RNA-DNA hybrid. In this experimental situation the RNA oligomer acts as a primer. Together with the template and polymerase it forms a structure that has been described as mimicking the elongation mode of transcription, however some of the properties of the polymerase enzyme may be slightly different under these conditions.

Here we report the incorporation of an rATP analog, 2'-(2-Nitrobenzyl)-ATP, into a growing RNA chain by complexes assembled according to Temiakov et al. This incorporation occurs as a non template-dependant addition of nucleotides to the 3' end of the RNA, and we have not observed this activity with elongation mode complexes on duplex DNA substrates. We suspect that this activity resembles the so-called 'N+1 effect', a phenomenon reported earlier for T7 RNA polymerase (Milligan).

Furthermore we provide evidence that the 2'-(2-Nitrobenzyl)-ATP acts as a terminator for further extension of the RNA chain by T7 RNA polymerase. We have used UV irradiation to remove the 2-nitrobenzyl moiety leaving a canonical 2'-OH group on the ribose ring of the terminal nucleotide. Transcription appears to be subsequently able to resume, thereby reversing the termination effect as desired for use in a sequencing methodology such as that which we have suggested.

Figure 4:
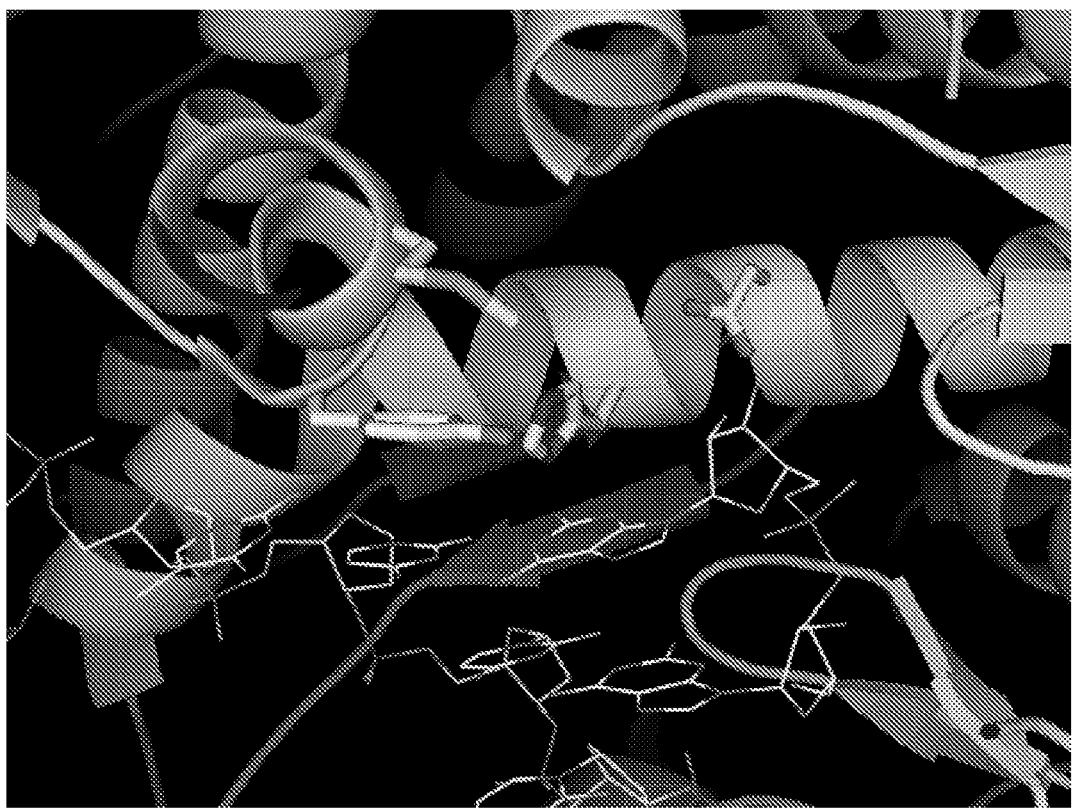
FIG. 4 depicts the catalytic site of the T7 polymerase.

The observation that nucleotides with a 2-Nitrobenzyl moiety at the 2' position can be incorporated into RNA by T7 RNA polymerase transcription complexes, even under unusual conditions, suggest a general limited degree of compatibility between these nucleotide analogs and the catalytic site of the enzyme not necessarily similar for other reagents. Indeed we have been unable to mimic such as effect with a similar compound in which the 3'-ribose position is modified instead. Crystal soaking studies of both Bst DNA polymerase (Johnson et al.) and T7 RNA polymerase (Yin and Steitz) reveal the protein/nucleotide motion during catalysis and provide some insight into the possible source of this observation. Most particularly they reveal that in addition to interactions favoring pre-catalytic binding of the nucleotide, the catalytic process also involves substantial motion of the protein and substrate during which the nucleotide is 'ratcheted' up until it is positioned deeper within a protein channel. During this complex motion the substrate nucleotide must move past a number of side chains, and notably the 3'-hydroxyl seems to move closely past a variety of residues during transit, and to sit snugly and tightly against the electron-density wall in the post-catalytic position. This suggests that placing bulky groups at the 3' position is likely to generate significant steric hindrance during a variety of stages of catalysis, and that identifying catalytically active (wild type or mutant) enzymes that incorporate bulky 3' groups is quite unlikely. Conversely, our catalysis data with the 2'-modified ATP supports the observation that this position is less obviously involved with contacting multiple amino acids in the active site during catalysis, and in particular appears to be positioned 'poking out' of the free channel after catalysis. This could provide the space for the bulky modification to sit without perturbing structure significantly, but would most likely impede binding and/or catalysis of the next incoming nucleotide, consistent with the observed chain-terminating behavior. Clearly the 2'-modified nucleotide is not free of inhibitory characteristics, but combining the known biochemical evidence, crystal structures, and our own data paves a way to a line of investigation in which a biochemical or genetic screen of mutants is undertaken to find T7 RNAP variants capable of incorporation of 2'-(2-Nitrobenzyl) ribonucleotides also in the processive mode of template dependant transcription. We can already identify the candidate amino acid residues that would be initially mutated to random variants singly, or in combination. These are lysine 631, methionine 635, tyrosine 639, and phenylalanine 644, all located on the nucleotide binding face of the 0 helix which shows the largest movement during catalysis (tyrosine 639 is already implicated in 2'-selection in T7 RNA polymerase (Brieba and Sousa. See also FIG. 4). On the 'back wall' of the binding pocket residues histidine 784 and aspartic acid 787 are obvious candidates for random mutagenesis (histidine 784 has also already been implicated in 2'-selection—Brieba and Sousa). Additionally we would consider substitutions of glycine 542 (the equivalent to the 'steric gate' in DNA polymerases inhibiting ribose incorporation, Gao et al.), and further deletions in this region. Finally, we could consider debulking the back pocket of the binding site, for example mutating residues 782, 783, 785, 786 to glycine or alanine. Any mutants that incorporate 2'-(2-Nitrobenzyl) ribonucleotides in the processive mode of template dependant transcription would be of great utility for the implementation of the novel single molecule sequencing technologies as proposed by our previous disclosure (Armes/Stemple patent application WO 00/53805). A similar approach may be taken with DNA polymerases, providing that some effort is first made to generally permit the access of ribose ands its possible derivatives by removing the steric gate (this involves mutating the structurally equivalent region to glycine 542 in T7 RNA polymerase, for example E710A in the *E. coli* klenow fragment. Astatke et al.). A polymerase with a steric gate deletion may include a deletion of an amino acid sequence comprising any one or more of the residues listed above. Similarly, a polymerase with amino acid substitutions in nucleotide binding and catalytic pocket may comprise a an amino acid substitution in any one or more of the residues listed above.

The nucleotides of the invention may be used for sequencing methods which involves single nucleic acid templates, such as those described in pending PCT application WO 00/53805. In addition, the nucleotides of the invention may be used for sequencing methods which involves multiple nucleic acid templates, such as, for example, pyrophosphate based sequencing method. In addition, the nucleotides of the invention may be substituted in any reaction where a terminating nucleotide is employed. For example, the nucleotides of the invention may be substitute for ddNTPs in sequencing by the Sanger method.

EXAMPLES

Example 1

Oligomers Used and Scaffold Formation

The nucleic acid scaffolds were formed by incubating 1 nmol RNA-1 (5'-biotin-AACUGCGGCGAU-3' (SEQ ID NO:1)) and 1 nmol DNA-1 (5'-GGGTCCTGTCT-GAAATACCTATCGCCGC-3' (SEQ ID NO:2)) in 100 µl transcription buffer (200 mM Tris-HCl (pH 7.9 at 25° C.), 30 mM MgCl$_2$, 50 mM DTT, 50 mM NaCl, 10 mM spermidine) for 10 minutes at 70° C. Annealing occurred by slowly lowering the temperature to 25° C. The concentration of hybrid was assumed to be 10 µM.

Example 2

Primer Extension Reactions

For the primer extension reactions 2 pmoles of scaffold were mixed with 10 units of T7 RNA polymerase (Fermentas) in 9 µl transcription buffer to allow the transcription complex to form. Reactions were started by the addition of 1 µl of 1 mM nucleotide solution and incubated for 20 minutes at 37°

C. Reactions were stopped by addition of 2 µl 500 mM EDTA and cooled on ice. UV irradiation was done for 10 minutes on a UV lamp.

Samples were precipitated, dissolved in formamide loading buffer and resolved on a denaturing 16% polyacrylamide gel (8M urea). Gels were electroblotted onto nylon-membrane (Osmonics, USA) in blotting buffer (0.5×TBE). Blots were incubated in blocking buffer (1×TBSTw/1% blocking reagent (Roche)) for 1 hour at room temperature to avoid non-specific noise, incubated with 0.5 µg/ml streptavidin-HRP (Sigma) in blocking buffer for 1 hour and washed extensively in Tris buffered saline containing 0.1% Tween-20. Detection was performed using a chemiluminescent substrate according to the instructions of the manufacturer (Pierce).

Example 3

Reversible Termination Reactions

For the reversible termination experiment 5 pmoles of scaffold were mixed with 6.5 pmoles of T7 RNA polymerase (possessing an N-terminal Histidine tag used in purification) in 180 µl transcription buffer to form active transcription complexes. The reaction was started by the addition of 20 µl of 10 mM 2'-(2-Nitrobenzyl)-ATP and incubated for 2 hours at 37° C. Subsequently the reaction was split into 4 samples and subjected to deprotection: two samples were exposed to UV irradiation as described above, two untreated samples were incubated for the same period of time at ambient temperature. Deprotection was followed by addition of 1 volume of either extension mix containing 250 µM rNTPs in transcription buffer, or addition of transcription buffer only. Samples were then incubated for another 1 hour at 37° C.

Processing, separation and detection of products was done as described above.

Example 4

Use of an RNA Oligomer of an RNA-DNA Hybrid Acts as Primer in the Scaffold Assay Temiakov et al. (Temiakov) have shown that a short RNA oligomer can serve as a primer for T7 RNA polymerase catalyzed transcription when hybridised to single-stranded DNA acting as a template. The polymerase can then be 'walked' along the coding template by the stepwise addition of cognate nucleotides. We confirmed these results, but observe that under the conditions used here additional nucleotides are incorporated in a non template dependent manner.

Figures 2A, 2B:
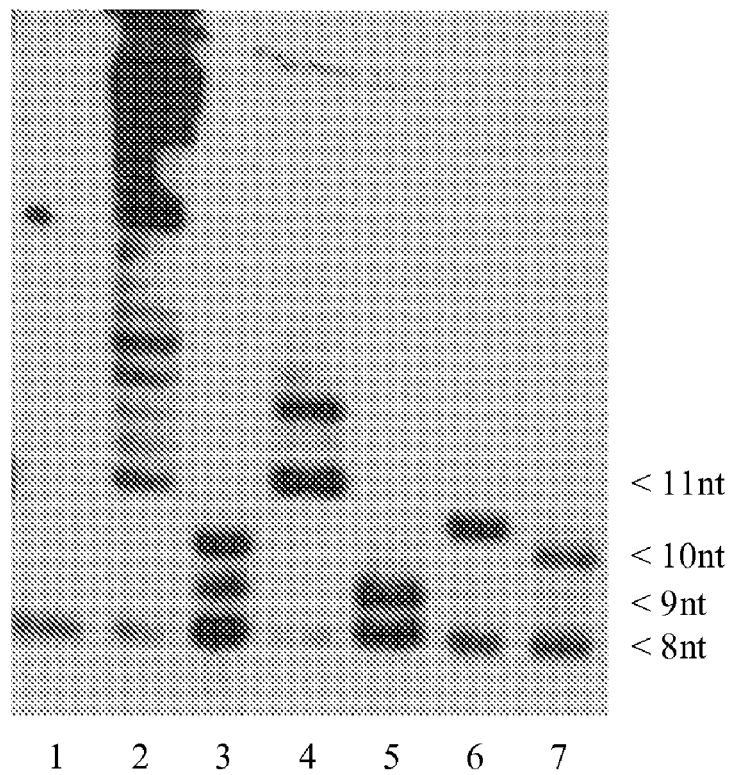
FIG. 2 (A) depicts a complex of an RNA oligomer and a single-stranded DNA template with 5' overhangs. The top strand is listed in the sequence listing as SEQ ID NO:1 and the bottom strand is listed in the sequence as SEQ ID NO:2; (B) depicts transcription products based on a template as depicted in (A).

An RNA oligomer and a single-stranded DNA template, such as those shown in FIG. 2A, can form a nucleic acid scaffold that interacts with T7 RNAP in a transcriptional complex. When presented with a cognate nucleotide (here rATP) the RNA primer is extended by one or two bases (FIG. 2B, lane 3). A scaffold will be extended by 3 or more bases (1B lane 4) when offered the next two nucleotides encoded by the DNA (here rATP and rGTP). If, on the other hand, the sole incoming nucleotide is non-cognate (here rCTP), the extension is limited to one base only (1B lane 5). The incorporation of one or more nucleotides in addition to the encoded base is evidently not a template dependant event. This effect is reminiscent of the so-called N+1 effect (Milligan).

The formation of a stable transcription complex by a RNA/DNA scaffold and T7 RNA polymerase offers a simple system for testing the potential of nucleotide analogs to be incorporated into a growing RNA chain.

Example 5

2'-(2 Nitrobenzyl-ATP is Incorporated into an RNA Chain by T7 RNA Polymerase

In this study we used 2'-(2-Nitrobenzyl)-ATP as a substrate for T7 RNA polymerase. The 2-Nitrobenzyl modification increases the molecular weight of the nucleotide analog and any nucleic acid into which the latter is incorporated. Consequently the electrophoretic mobility of an RNA containing a NB-moiety is altered correspondingly, allowing modified transcripts to be identified. Due to the nature of its preparation, the 2'-(2-Nitrobenzyl)-ATP used in this experiment is contaminated with rATP by an estimated 5% (see Materials and Methods).

As shown in FIG. 2B, lane 6, the mobility of the main product of a reaction containing predominantly 2'-(2-Nitrobenzyl)-ATP appears to migrate at a position between 10 nucleotides and 11 nucleotides of unmodified RNA (compare to lanes 3 and 4). This product of intermediate molecular weight suggests the incorporation of at least one 2-nitrobenzyl-modified nucleotide.

How many 2'-(2-Nitrobenzyl)-ATP nucleotides per molecule have been incorporated? A faint band at the 9 nucleotide position (compare lane 6 and 7) signifies that contaminating unmodified rATP has also been utilized (note that the concentration of rATP will be around 5 µM; even at this low concentration it can be readily used by the T7 RNAP (Song)). The absence of any product of 10 nucleotides in length rules out the possibility that any unmodified rATP has been incorporated in an N+1 type activity (as was the case at high rATP concentrations; see lane 6). The main product could be the result of the incorporation of a single 2'-(2-Nitrobenzyl)-ATP, of two 2'-(2-Nitrobenzyl)-ATP (the second of which would be non-template dependant, i.e. N+1 type), or of one 2'-(2-Nitrobenzyl)-ATP added to a canonically incorporated rATP. Further evidence for the identity of the main product of transcription in the presence of high concentrations of 2'-(2-Nitrobenzyl)-ATP comes from a deprotection experiment.

Example 6

Deprotection of 2'-(2-Nitrobenzyl)-ATP by UV Light

The 2-Nitrobenzyl moiety is a photolabile group used in many application for its ability to absorb light energy and cleave the covalent bond between itself and a 'protected' molecule (Givens). In the case of 2'-(2-Nitrobenzyl)-modified nucleotides, cleavage of this bond generates a free 2'-OH group on the ribose ring. The product of this photo-deprotection should consequently run at the same position as an RNA oligomer extended by the incorporation of unmodified rATP.

As shown in FIG. 2B, lane 7, UV treatment of the main product of 2'-(2-Nitrobenzyl)-ATP incorporation leads to an increase of its electrophoretic mobility. The main band now runs at the same position as an RNA of 10 nt in length (compare lane 3 and 7). This observation confirms the notion of 2'-(2-Nitrobenzyl)-ATP incorporation into the nascent RNA chain by T7 RNAP (unmodified RNA oligomers do not alter their electrophoretic mobility in response to UV treatment; data not shown). It also allows us to rule out one of the above-mentioned alternatives for the composition of the main product of 2'-(2-Nitrobenzyl)-ATP incorporation:

The incorporation of a single 2'-(2-Nitrobenzyl)-ATP should lead to a loss of any band greater than 9 nucleotides and an increase in intensity of the 9 nucleotide band as a response to UV treatment. Since neither is the case, this possibility can be discarded.

Does the main product contain one 2'-(2-Nitrobenzyl)-ATP incorporated in the N+1 mode of T7 RNAP activity (succeeding a cognate rAMP), or two 2'-(2-Nitrobenzyl)-ATPs? Although the experimental results presented so far cannot formally distinguish between these two possibilities, the latter alternative requires two assumptions to be made which render it much less likely.

Firstly, the incorporation of 2'-(2-Nitrobenzyl)-ATP would have to be far more efficient than that of rATP, i.e. the modified nucleotide would have to be the better substrate. Offering 2'-(2-Nitrobenzyl)-ATP does not result in the formation of any oligomers with only a single incorporated modified ATP (which would have to run at a position between 9 and 10 nucleotides in length; 1B, lane 6) suggesting that any incorporation of one 2'-(2-Nitrobenzyl)-ATP is necessarily followed by the addition of a second (N+1 type activity) modified nucleotide. When, on the other hand, the transcription complex is presented with unmodified rATP only, the product of the reaction is a mixture of RNA oligomers extended by one or two nucleotides (FIG. 2B, lane 4).

Secondly, the 3'-OH group of a terminal 2'-(2-Nitrobenzyl)-ATP in a nascent RNA chain would still have to be a target for 17 RNA polymerase dependent extension, i.e. 2'-(2-Nitrobenzyl)-ATP would have to be non-terminator. The latter requirement has been addressed in an additional experiment.

Example 7

2'-(2-Nitrobenzyl)-ATP Acts as Reversible Terminator of Transcription

A potential application for the incorporation of NB-modified nucleotides by a polymerase is their use as reversible terminators in a novel sequencing technology (WO 00/53805). We therefore examined the ability of 2'-(2-Nitrobenzyl)-ATP to act as a terminator of transcription.

Figure 3:
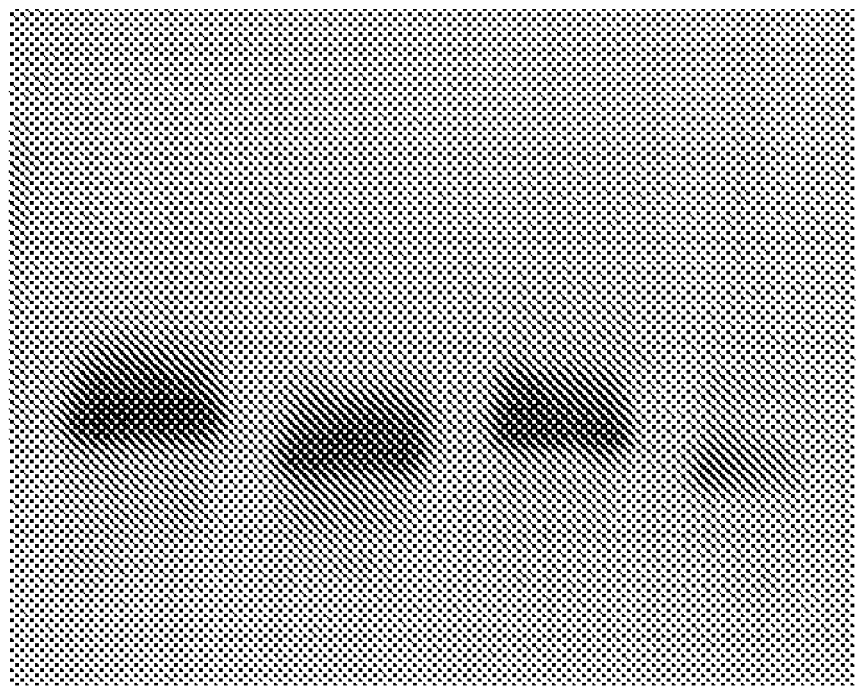
FIG. 3 depicts transcription experiments using the nucleotides of the invention.

In the experiment shown in FIG. 3 scaffolds where incubated with T7 RNAP and 2'-(2-Nitrobenzyl)-ATP. As in the experiment described earlier the product of such a reaction has an apparent electrophoretic mobility that lies between those of oligomers of 10 and 11 nucleotides (FIG. 3, lane 1). When subjected to UV irradiation, the NB moiety incorporated into the RNA is removed and the mobility of the product increases to that of a 10 nucleotide oligomer (FIG. 3, lane 2). Transcription can resume upon the addition of unmodified rNTPs. When the 2-Nitrobenzyl moiety of the terminal base nucleotide has been removed by photodeprotection, this leads to a decrease in signal intensity of the main band, presumably because the product is being extended (FIG. 3, lane 4). In contrast, RNA chains still bearing the Nitrobenzyl group can not be extended by the transcription complex, and the amount of product remains effectively unchanged (FIG. 3, lane 3). We note that complete utilisation of the deprotected material has not occurred. This may be the case for a variety of reasons including the fact that the polymerase will necessarily have to extend from a mismatch in these 'chase' experiments. Nevertheless the data is best explained we believe by the suggestion that the 2'-(2-Nitrobenzyl)-ATP has functioned as a terminator, which can be reversed on deprotection.

In conclusion, we have shown that 2'-(2-Nitrobenzyl)-ATP acts as a bona fide terminator of transcription. Elongation of the transcript can resume upon removal of the protecting 2-Nitrobenzyl group by UV irradiation. This quality of the 2'-(2-Nitrobenzyl)-ATP also rules out the possibility mentioned above that the main product of transcription in presence of high concentrations of 2'-(2-Nitrobenzyl)-ATP could be an RNA primer extended by two rather than one modified nucleotide.

All patents, patent applications, and references cited in this specification is hereby incorporated by reference.

REFERENCES

Armes N, Stemple D L; PCT application WO 00/53805.
Astatke M, Ng K, Grindley N D F, Joyce C M; *Proc Natl Acad Sci U.S.A.* (1998) 95:3402-3407
Brieba L G, Sousa R; *Biochemistry*. (2000) February 8; 39(5):919-23
Cech T R; *The RNA World*. Cold Spring Harbor Laboratory Press. 1993; 239-269.
Conrad F, Hanne A, Gaur R K, Krupp G; *Nucleic Acids Res*. (1995) 23:1845-53.
Gao G, Orlava M, Georgiadis M, Hendrickson W, Goff S; *Proc Natl Acad Sci U.S.A.* (1997) 94:407-411
Givens R S, Weber J F, Jung A H, Park C H; *Methods Enzymol*. (1998) 291:1-29.
Johnson S J, Taylor J S, Beese L S; *Proc Nat Acad Sci U.S.A.* (2003) 100(7):3895-3900
Milligan J F, Groebe D R, Witherell G W, Uhlenbeck O C; *Nucleic Acids Res*. (1987) 15:8783-98.
Padilla R, Sousa R; *Nucleic Acids Res*. (2002) 30:e138.
Raap A K; *Mutat. Res*. (1998) 400:287-298.
Sanger F, Nicklen S, Coulson A R; *Proc Natl Acad Sci U.S.A.* (1977) 74:5463-7.
Sioud M, Sorensen D R; *Natl. Biotechnol*. (1998) 16:556-61.
Song H, Kang C; *Genes Cells*. (2001) 6:291-301.
Tabor S, Richardson C C; *Proc. Natl. Acad. Sci. U.S.A.* (1995) 92:6339-43.
Temiakov D, Anikin M, McAllister W T; *J. Biol. Chem.* (2002) 277:47035-43.
Yin Y W, Steitz T A; *Cell* (2004) February 6; 116(3):393-404.

We claim:

1. A ribonucleotide having a formula PM-SM-BASE wherein PM is a phosphate moiety, SM is a ribose, BASE is a pyrimidine or purine, and wherein said ribose comprises a reversible chain terminating moiety at a 2' position in said ribose, wherein the reversible chain terminating moiety is selected from the group consisting of a 2-Nitrobenzyl group, a Desyl group and a p-hydroxyphenacyl caging group.

2. The ribonucleotide of claim 1 wherein the BASE is selected from the group consisting of adenine, guanine, cytosine and uracil.

3. The ribonucleotide of claim 1 which is a ribonucleoside 5'-phosphate.

4. The ribonucleotide of claim 1 wherein said reversible chain terminating moiety is connected to said ribose by a reversible linkage.

5. The ribonucleotide of claim 4 wherein said reversible linkage is a bond that is cleavable by electromagnetic radiation, chemical treatment, or a combination thereof.

6. The ribonucleotide of claim 5 wherein said electromagnetic radiation is light.

7. The ribonucleotide of claim 1 wherein the reversible chain terminating moiety is a 2-Nitrobenzyl group.

8. The ribonucleotide of claim 1 wherein the reversible chain terminating moiety is a Desyl group.

9. The ribonucleotide of claim 1 wherein the reversible chain terminating moiety is a p-hydroxyphenacyl caging group.

10. The ribonucleotide of claim 1 wherein said ribonucleotide is labeled with a detectable label.

11. The ribonucleotide of claim 10 wherein said detectable label is a moiety is selected from the group consisting of green fluorescent protein, blue fluorescent protein, red fluorescent protein, beta-galactosidase, chloramphenicol acetyltransferase, beta-glucoronidase, luciferases, beta-lactamase, digoxygenin, fluorescent dye molecule, fluorescein, alkaline phosphatase and horse radish peroxidase.

12. The ribonucleotide of claim 10 wherein said detectable label may be removed by photobleaching.

13. The ribonucleotide of claim 10 wherein said detectable label is connected to the ribonucleotide by a reversible linkage.

14. A method of producing a reversibly terminating ribonucleoside comprising:
(a) providing a ribonucleoside having a formula SM-BASE wherein SM is a ribose, BASE is a pyrimidine or purine, wherein the ribonucleoside comprises a detectable label; and
(b) attaching a reversible chain terminating moiety at a 2' position of said ribose, wherein said reversible chain terminating moiety is selected from the group consisting of a 2-Nitrobenzyl group, a Desyl group and a p-hydroxyphenacyl caging group.

15. A method of sequencing a target nucleic acid comprising:
(a) elongating a primer which is complexed with a target nucleic acid to form an incorporated ribonucleotide with a RNA polymerase and at least one first species of ribonucleotide having the formula PM-SM-BASE wherein PM is a phosphate moiety, SM is a ribose, BASE is a pyrimidine or purine, wherein said ribose comprises a chain terminating moiety connected by a reversible linkage at a 2' position of said ribose, wherein said reversible chain terminating moiety is selected from the group consisting of a 2-Nitrobenzyl group, a Desyl group and a p-hydroxyphenacyl caging group, and wherein the at least one first species of ribonucleotide comprises a detectable label; and
(b) detecting said incorporated ribonucleotide to determine a sequence of said target nucleic acid.

16. The method of claim 15 further comprising:
(c) removing said chain terminating moiety of said incorporated ribonucleotide by breaking said reversible linkage;
(d) repeating steps (a), (b) and (c) with at least one second species of ribonucleotide having the formula PM-SM-BASE wherein PM is a phosphate moiety, SM is a ribose, BASE is a pyrimidine or purine, wherein said ribose comprises a chain terminating moiety connected by a reversible linkage at a 2' position of said ribose, wherein said reversible chain terminating moiety is selected from the group consisting of a 2-Nitrobenzyl group, a Desyl group and a p-hydroxyphenacyl caging group.

17. The method of claim 15 wherein said complex between said primer and said target nucleic acid is formed by hybridization or synthesis by RNA polymerase.

18. The method of claim 15 wherein said RNA polymerase is a phage-encoded RNA polymerase selected from the group consisting of T3 RNA polymerase, T7 RNA polymerase and SP6 RNA polymerase.

19. The ribonucleotide of claim 1 which is a ribonucleoside 5'-diphosphate.

20. The ribonucleotide of claim 1 which is a ribonucleoside 5'-triphosphate.

21. The ribonucleotide of claim 1, wherein the BASE is adenine or guanine, and wherein the PM is a monophosphate, diphosphate, or triphosphate moiety.

22. The ribonucleotide of claim 1, wherein the BASE is uracil or cytosine, and wherein the PM is a monophosphate, diphosphate, or triphosphate moiety.

23. The ribonucleotide of claim 13, wherein the reversible linkage is a bond that is cleavable by electromagnetic radiation, chemical treatment, or a combination thereof.

* * * * *

UNITED STATES PATENT AND TRADEMARK OFFICE
CERTIFICATE OF CORRECTION

PATENT NO. : 8,022,194 B2  
APPLICATION NO. : 12/803261  
DATED : September 20, 2011  
INVENTOR(S) : Olaf Piepenburg Page 1 of 1

It is certified that error appears in the above-identified patent and that said Letters Patent is hereby corrected as shown below:

IN THE SPECIFICATIONS:

Column 1,
Line 9, Delete "PCT/1B2005/002488," and insert --PCT/IB2005/002488,--

IN THE CLAIMS:

Column 11,
Line 31, Claim 3, Delete "5 '-phosphate." and insert --5'-phosphate.--

Column 11,
Line 54, Claim 11, Delete "beta-glucoronidase," and insert --beta-glucuronidase,--

Column 11,
Line 55, Claim 11, Delete "digoxygenin," and insert --digoxigenin,--

Signed and Sealed this
Twenty-ninth Day of November, 2011

David J. Kappos
*Director of the United States Patent and Trademark Office*

SEQUENCE LISTING

<160> NUMBER OF SEQ ID NOS: 2

<210> SEQ ID NO 1
<211> LENGTH: 12
<212> TYPE: RNA
<213> ORGANISM: Artificial Sequence
<220> FEATURE:

-continued

```
<223> OTHER INFORMATION: Oligomer

<400> SEQUENCE: 1
aacugcggcg au                                                              12

<210> SEQ ID NO 2
<211> LENGTH: 28
<212> TYPE: DNA
<213> ORGANISM: Artificial Sequence
<220> FEATURE:
<223> OTHER INFORMATION: Oligonucleotide

<400> SEQUENCE: 2
gggtcctgtc tgaaatacct atcgccgc                                             28
```